US012612628B2

(12) United States Patent
Yim et al.

(10) Patent No.: US 12,612,628 B2
(45) Date of Patent: Apr. 28, 2026

(54) COMPOSITION FOR TREATING METASTATIC SOLID CANCER, COMPRISING TSG6 INHIBITOR

(71) Applicant: Industry-University Cooperation Foundation Hanyang University Erica Campus, Ansan-si (KR)

(72) Inventors: Hyung Shin Yim, Seoul (KR); Sol-Bi Shin, Ansan-si (KR); Hay-Ran Jang, Ansan-si (KR)

(73) Assignee: Industry-University Cooperation Foundation Hanyang University Erica Campus, Ansan-si (KR)

( * ) Notice: Subject to any disclaimer, the term of this patent is extended or adjusted under 35 U.S.C. 154(b) by 473 days.

(21) Appl. No.: 18/010,832

(22) PCT Filed: Jun. 16, 2021

(86) PCT No.: PCT/KR2021/007552
§ 371 (c)(1),
(2) Date: Dec. 16, 2022

(87) PCT Pub. No.: WO2021/256855
PCT Pub. Date: Dec. 23, 2021

(65) Prior Publication Data
US 2024/0263175 A1 Aug. 8, 2024

(30) Foreign Application Priority Data
Jun. 16, 2020 (KR) ........................ 10-2020-0072862

(51) Int. Cl.
*C12N 15/113* (2010.01)
*A61P 35/04* (2006.01)

(52) U.S. Cl.
CPC ............ *C12N 15/113* (2013.01); *A61P 35/04* (2018.01); *C12N 2310/11* (2013.01); *C12N 2310/14* (2013.01); *C12N 2310/141* (2013.01); *C12N 2310/16* (2013.01); *C12N 2310/531* (2013.01)

(58) Field of Classification Search
None
See application file for complete search history.

(56) References Cited

U.S. PATENT DOCUMENTS 7,452,667 B2 11/2008 Liew et al.
2010/0093552 A1* 4/2010 Panja ............... G01N 33/57446
506/7

FOREIGN PATENT DOCUMENTS

WO WO 2009/125303 10/2009

OTHER PUBLICATIONS

International Search Report and the Written Opinion Dated Sep. 27, 2021 From the International Searching Authority Re. Application No. PCT/KR2021/007552 and Its Translation of Search Report Into English. (14 Pages).
Chen et al. "*Homo Sapiens* TNF Alpha Induced Protein 6 (TNFAIP6), mRNA", Database NCBI [Online], NCBI Reference Sequence: NM_007115.4, Database Accession No. NM_007115, 4 P., Feb. 26, 2024.
Shin et al. "Active PLK1-Driven Metastasis Is Amplified by TGF-Beta Signaling That Forms a Positive Feedback Loop in Non-Small Cell Lung Cancer", Oncogene, 39(4): 767-785, Published Online Sep. 23, 2019.
Zhang et al. "Seeking for Correlative Genes and Signaling Pathways With Bone Metastasis From Breast Cancer by Integrated Analysis", Frontiers in Oncology, 9: 138-1-138-13, Mar. 13, 2019.

* cited by examiner

*Primary Examiner* — Tracy Vivlemore

(57) ABSTRACT
The present invention relates to a use of TSG6 shRNA as a therapeutic agent for metastatic solid cancer. More specifically, the present invention can be usefully used for treating cancer in which metastasis occurs by PLK1, which is known to be overexpressed, particularly in cancer, and the active form thereof or TGF-beta/Smad signaling by reducing proliferation, migration, and invasiveness of metastatic cancer cells through gene therapy that suppresses TSG6 mRNA expression.

6 Claims, 5 Drawing Sheets
Specification includes a Sequence Listing.

Homo sapiens TNF alpha induced protein 6 (TNFAIP6), mRNA. [NM_007115.4]

```
   1 agtcacatt  cagccactgc  tctgagaatt  tgtgagcagc  ccctaacagg  ctgttacttc
  61 actacaactg  acgatatgat  catcttaatt  tacttatttc  tcttgctatg  ggaagacact
 121 caaggatggg  gattcaagga  tggaattttt  cataactcca  tatggcttga  acgagcagcc
 181 ggtgtgtacc  acagagaagc  acggtctggc  aaatacaagc  tcacctacgc  agaagctaag
 241 gcggtgtgtg  aatttgaagg  cggccatctc  gcaacttaca  agcagctaga  ggcagccaga
 301 aaaattggat  ttcatgtctg  tgctgctgga  tggatggcta  agggcagagt  tggatacccc
 361 attgtgaagc  cagggcccaa  ctgtggattt  ggaaaaactg  gcattattga  ttatggaatc
 421 cgtctcaata  ggagtgaaag  atgggatgcc  tattgctaca  acccacacgc  aaaggagtgt
 481 ggtggcgtct  ttacagatcc  aaagcaaatt  tttaaatctc  caggcttccc  aaatgagtac
 541 gaagataacc  aaatctgcta  ctggcacatt  agactcaagt  atggtcagcg  tattcacctg
 601 agttttttag  attttgacct  tgaagatgac  ccaggttgct  tggctgatta  tgttgaaata
 661 tatgacagtt  acgatgatgt  ccatggcttt  gtgggaagat  actgtggaga  tgagcttcca
 721 gatgacatca  tcagtacagg  aaatgtcatg  accttgaagt  ttctaagtga  tgcttcagtg
 781 acagctggag  gtttccaaat  caaatatgtt  gcaatggatc  ctgtatccaa  atccagtcaa
 841 ggaaaaaata  caagtactac  ttctactgga  aataaaaact  ttttagctgg  aagatttagc
 901 cacttataaa  aaaaaaaaaa  aggatgatca  aaacacacag  tgtttatgtt  ggaatctttt
 961 ggaactcctt  tgatctcact  gttattatta  acatttattt  attattttc  taaatgtgaa
1021 agcaatacat  aatttaggga  aaattggaaa  atataggaaa  ctttaaacga  gaaaatgaaa
1081 cctctcataa  tcccactgca  tagaaataac  aagcgttaac  attttcatat  ttttttcttt
1141 cagtcatttt  tctatttgtg  gtatatgtat  atatgtacct  atatgtattt  gcattgaaa
1201 ttttggaatc  ctgctctatg  tacagttttg  tattatactt  tttaaatctt  gaactttata
1261 aacattttct  gaaatcattg  attattctac  aaaaacatga  ttttaaacag  ctgtaaaata
1321 ttctatgata  tgaatgtttt  atgcattatt  taagcctgtc  tctattgttg  gaatttcagg
1381 tcattttcat  aaatattgtt  gcaataaata  tccttgaaca  ca /
```

COMPOSITION FOR TREATING METASTATIC SOLID CANCER, COMPRISING TSG6 INHIBITOR

RELATED APPLICATIONS

This application is a National Phase of PCT Patent Application No. PCT/KR2021/007552 having International filing date of Jun. 16, 2021, which claims the benefit of priority of Korea Patent Application No. 10-2020-0072862 filed on Jun. 16, 2020. The contents of the above applications are all incorporated by reference as if fully set forth herein in their entirety.

SEQUENCE LISTING STATEMENT

The ASCII file, entitled 94729SequenceListing.txt, created on Dec. 16, 2022, comprising 4,575 bytes, submitted concurrently with the filing of this application is incorporated herein by reference. The sequence listing submitted herewith is identical to the sequence listing forming part of the international application.

FIELD AND BACKGROUND OF THE INVENTION

The present invention relates to a composition for treating metastatic solid cancer, including a TSG6 inhibitor.

Anti-inflammatory responses are known to suppress immune responses in cancer, promote the growth of cells, and induce metastasis. Tumor necrosis factor-α (TNF-α), known as a cytokine of an inflammatory response, is usually secreted by macrophages, T-cells (helper T cells), and natural killer (NK) cells, and the normal secretion of TNF-α induces apoptosis and suppresses tumorigenesis. Tumor necrosis factor-inducible gene 6 protein (TSG6) is an anti-inflammatory protein induced by such TNF-α, and inhibits the stimulation of TNF-α to regulate each other's signaling system.

The anti-inflammatory factor TSG6 is usually expressed in mesenchymal stromal cells (MSCs), and is known to suppress T cell function and promote the proliferation of cells. Further, TSG6 binds to hyaluronic acid, is involved in the stabilization of an extracellular matrix, and induces the migration of cells. In addition, it has been reported that TSG6 also integrally binds to substrate-associated molecules such as fibronectin, which is known as a mesenchymal cell marker, to promote the migration of cells. Recently, it has been researched that TSG6 reduces immune responses in cartilage protection in arthritis, xeroma, retinal transplantation or transplantation of organs such as the kidneys and liver to help stabilize the transplanted organ.

Polo-like kinase 1 (PLK1) has recently been researched as a target molecule responsible for carcinogenesis and metastasis, and based on this research, research on the development of anti-cancer drugs through the development of inhibitors against PLK1 has been conducted in various fields. PLK1 is, as a serine threonine kinase, an enzyme which induces phosphorylation of Ser/Thr residues of a substrate by binding an activated PLK1 form to the substrate and a polo-box domain.

Functionally, expression is increased in growing and dividing cells, but the expression and activity peak particularly in the mitotic phase of the cell cycle. Therefore, it is known that its expression rate is also high in rapidly growing cancer cells, and the team of the present invention discovered that the metastasis of cancer is promoted by activating TGF-β signaling.

Although cancer metastasis is a phenomenon that occurs as a result of cancer progression, the survival rate is excessively decreased due to cancer recurrence, and the like when metastasis cannot be prevented even though the primary cancer is virtually eliminated or treated. Although it is thought that the larger the size of cancer, the higher the rate of metastasis to surrounding lymph nodes and other tissues, cancer may metastasize even though the size of the cancer is small, so that the relationship between cancer metastasis and proliferation has not yet been clearly elucidated. In cancer treatment, suppression of cancer cell proliferation and suppression of cancer cell metastasis are not effects that always occur together, and in terms of the fact that the treatment efficiency of many cancers can be dramatically improved when the metastasis of cancer can be suppressed, there is a need for developing a therapeutic target or therapeutic agent that effectively suppresses cancer metastasis and invasion for the treatment of metastatic cancer.

SUMMARY OF THE INVENTION

An object of the present invention is to provide a use of treating metastatic solid cancer based on gene therapy that suppresses TSG6 expression.

To achieve the object, the present invention provides a composition for treating metastatic solid cancer, including a tumor necrosis factor-inducible gene 6 protein (TSG6) inhibitor that targets the base sequence of SEQ ID NO: 1 or 2.

The present invention also provides a use of a TSG6 inhibitor that targets the base sequence of SEQ ID NO: 1 or 2 for preparing a medicament for treating metastatic solid cancer.

The present invention also provides a method for treating metastatic solid cancer, the method including administering a therapeutically effective amount of a TSG6 inhibitor that targets the base sequence of SEQ ID NO: 1 or 2 to a subject in need thereof.

The present invention can be usefully used for treating cancer in which metastasis occurs by PLK1, which is known to be overexpressed, particularly in cancer, and the active form thereof or TGF-beta/Smad signaling by reducing proliferation, migration, and invasiveness of metastatic cancer cells through gene therapy that suppresses TSG6 expression.

BRIEF DESCRIPTION OF THE SEVERAL VIEWS OF THE DRAWINGS

FIG. 2 shows the results of observing cancer cell migration when cancer cells expressing the active form of PLK1 (TD-PLK1) were treated with TSG6 and observing changes in cancer cell migration when treated with TSG6 in an environment treated with a metastasis inducer TGF-β.

A shows the results of analyzing gene expression patterns according to the TNFAIP6 expression in general tissues, cancer tissues (Tumor stage 1), and cancer tissues with metastatic potential (Tumor stage 2-4) of cancer patients using Morpheus program (website software (dot)broadinstitute(dot)org/morpheus/) capable of drawing heat maps, and B shows the results illustrating changes in expression of Smad2/3, which is a main protein of the TGF-β signaling pathway, and phosphorylated and activated Smad2 together with changes in expression of TSG6, a PLK1 active form (TD-PLK1), PLK1, epithelial-mesenchymal transition markers (E-cadherin, N-cadherin) and CD44 protein when lung cancer cells are treated with TSG6.

C is a graph showing the expression patterns of epithelial-mesenchymal transition markers (epithelial marker, CDH1; mesenchymal marker, CDH2), TGFB1, and PLK1 mRNA when lung cancer cells are treated with TSG6, and D is a graph showing a pattern in which cancer cell migration induced by PLK1 active form (TD-PLK1) is further increased by treatment with TSG6.

E is a graph showing a pattern in which cancer cell migration induced by a metastasis inducer TGF-β is further increased by treatment with TSG6.

Figure 3:
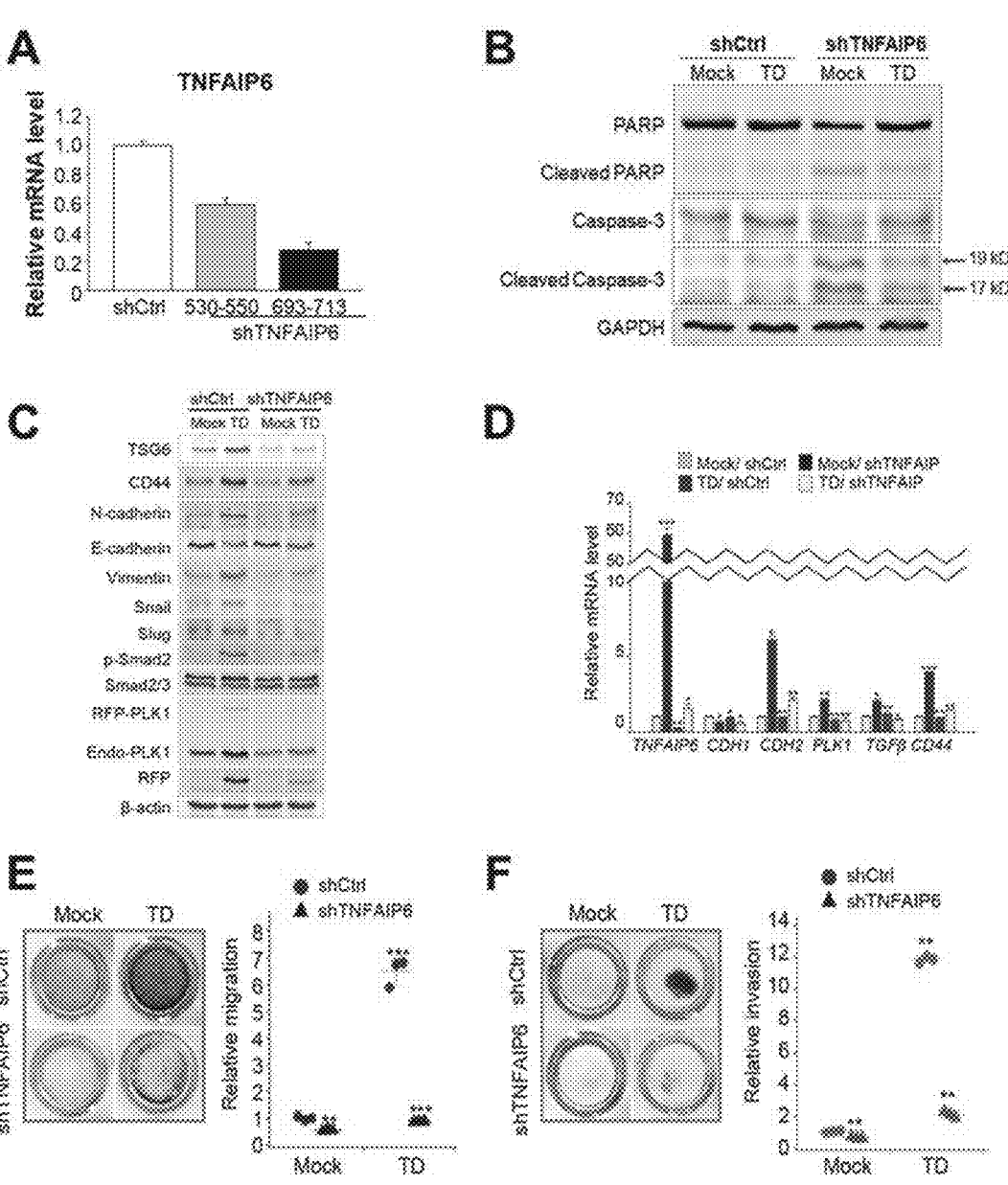
Figure 4:
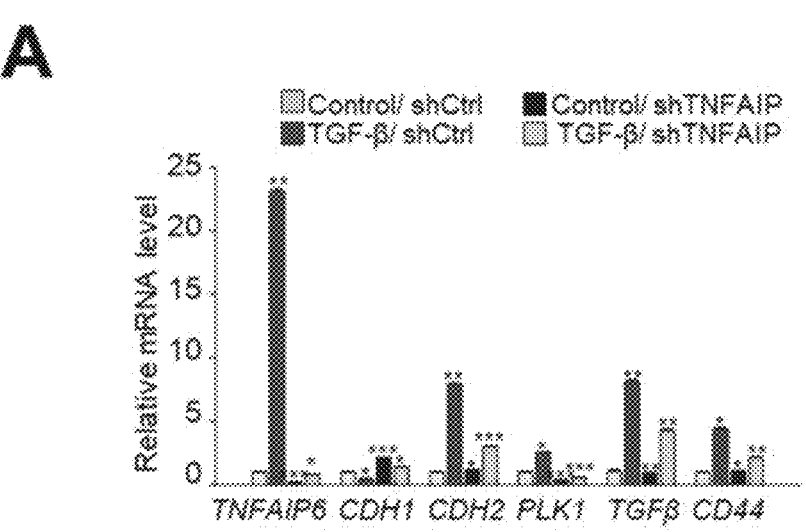
Figure 4:
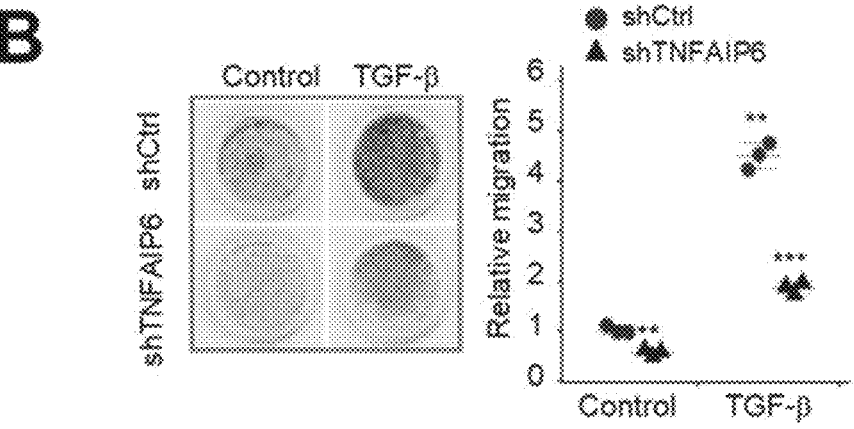
Figure 4:
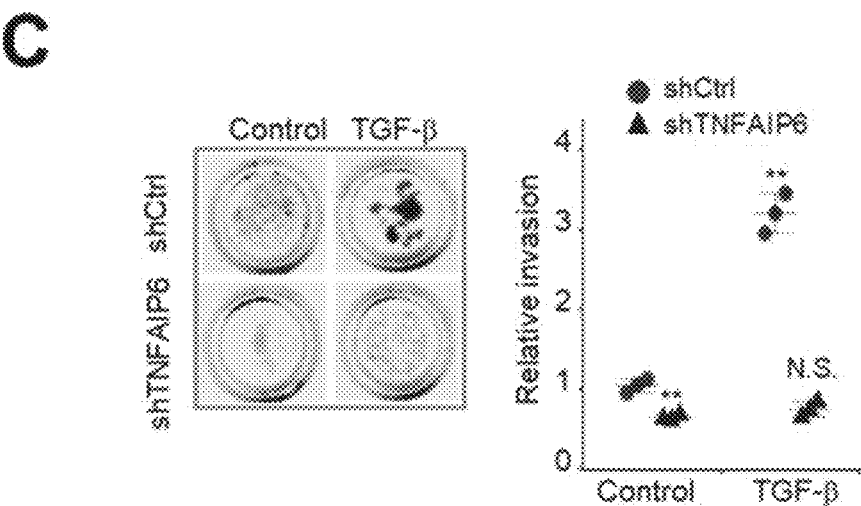

FIG. 3 shows the results of confirming the effect of suppressing the metastasis of cancer cells by treatment with TSG6 shRNA, which is a TSG6 mRNA expression inhibitory material, in active form PLK1-expressing cancer cells according to exemplary embodiments of the present invention, A is a graph of measuring the degree of TSG6 expression inhibition of TSG6 shRNA according to a target sequence using real-time polymerase chain reaction (real-time PCR), B shows the results of observing, by immunoblotting using cleaved caspase-3 and cleaved PARP antibodies, cancer cell death by shRNA treatment of TSG6 in a metastatic environment in which active form PLK1 is expressed, C shows the results of observing, by immunoblotting, changes in protein expression of epithelial-mesenchymal transition markers, Smad2/3, which is a main protein of the TGF-β signaling pathway, and activated p-Smad2 by shRNA treatment of TSG6 in a metastatic environment in which active PLK1 is expressed, D shows the results of observing, by real-time polymerase chain reaction (real-time PCR), changes in epithelial-mesenchymal transition markers at mRNA levels by shRNA treatment of TSG6 in a metastatic environment in which active form PLK1 is expressed, E is a graph showing the degree of migration in an experimental group as a relative ratio when the degree of migration of cells in which a control vector (pLKO-puro1.) is infected with a virus is set to 1 in cell migration assay experiments using inserts, and F is a graph showing the degree of invasiveness in another experimental group as a relative ratio when the degree of migration of cells in which a control vector is infected with a pLKO-Puro virus is set to 1 in cell migration assay experiments using Matrigel, FIG. 4 shows the results of observing changes in epithelial-mesenchymal transition markers and changes in cancer migration and invasiveness when treated with TSG6 shRNA, which is a TSG6 mRNA expression inhibitor, in an environment treated with TGF-β, which is known to induce metastasis, A is a graph showing mRNA expression patterns of epithelial-mesenchymal transition markers (CDH1, CDH2) and PLK1, TGF-β, and CD44 when cancer cell metastasis induced by TGF-β treatment is treated with TSG6 shRNA, which is a TSG6 mRNA expression inhibitor, B is a graph showing a pattern in which cancer cell migration induced by TGF-β treatment is reduced by TSG6 shRNA treatment, and C is a graph showing a pattern in which cancer cell invasiveness induced by TGF-β treatment is reduced by TSG6 shRNA treatment.

FIG. 5 illustrates the gene sequence of TNF-α stimulated gene 6, Human TSG6 mRNA [NM_007115.4] (TSG6) (SEQ ID NO: 7).

DETAILED DESCRIPTION OF SPECIFIC EMBODIMENTS OF THE INVENTION

Hereinafter, the configuration of the present invention will be described in detail.

The present invention relates to a composition for treating metastatic solid cancer, including a TSG6 inhibitor that targets the base sequence of SEQ ID NO: 1 or 2.

Further, the present invention provides a use of a TSG6 inhibitor that targets the base sequence of SEQ ID NO: 1 or 2 for preparing a medicament for treating metastatic solid cancer.

TSG6 is known to suppress T-cell function and promote cell proliferation by inhibiting TNF-α stimulation. In addition, it has been reported that TSG6 binds to hyaluronic acid, is involved in the stabilization of an extracellular matrix, induces the migration of cells, and also integrally binds to matrix-associated molecules such as fibronectin, which is known as a mesenchymal cell marker, to promote the migration of cells. However, the use of TSG6 expression inhibition for reducing the metastasis of cancer cells has not been clarified. The present inventors have newly revealed that the expression of mRNA and/or protein of TSG6 can be inhibited to improve or treat metastasis, migration and invasion of cancer cells. According to an exemplary embodiment of the present invention, it was confirmed that TSG6 is suitable as a therapeutic target for metastatic cancer by confirming that when the expression of mRNA is inhibited using shRNA that inhibits the expression of TSG6 mRNA, the migration and invasiveness of cancer cells are reduced.

In the present invention, "TSG6 inhibitor" generally refers to all agents that reduce the expression or activity of TSG6 mRNA or the TSG6 protein, and specifically, may include all agents that interfere with the expression of TSG6 at the transcriptional level to reduce the expression of TSG6. In the present invention, "TSG6" may be interpreted to refer to both TSG6 mRNA and protein unless otherwise specified. Preferably, TSG6 may target the base sequence 530-550 (SEQ ID NO: 1) and the base sequence 693-713 (SEQ ID NO: 2) of human TSG6 mRNA [NM_007115.4] (SEQ ID NO:7) and complementarily bind to the sequences to inhibit TSG6 mRNA expression.

An inhibitor that inhibits the expression of the TSG6 mRNA may be any one of siRNA, shRNA, miRNA, an antisense oligonucleotide or an aptamer, which specifically binds to the target sequence.

In the present invention, the terms "siRNA" and "shRNA" can inhibit the expression of target genes as nucleic acid molecules capable of mediating RNA interference or gene silencing, and thus are used as efficient gene knockdown methods or gene therapeutic methods. shRNA has a hairpin structure formed by binding between complementary sequences within a single-stranded oligonucleotide, and in vivo, the shRNA is cleaved by dicer to become siRNA, which is a double-stranded oligonucleotide, as a small RNA fragment of 8 to 30 nucleotides in size, and may bind specifically to mRNA with a complementary sequence to inhibit expression. Therefore, which one of shRNA and siRNA to be used may be determined by those skilled in the art, and when shRNA and siRNA target the same mRNA sequence, a similar expression-reduction effect may be expected.

For the purpose of the present invention, TSG6 may be inhibited by specifically acting on TSG6 to cleave TSG6 mRNA molecules, thereby inducing an RNA interference (RNAi) phenomenon. siRNA may be chemically or enzymatically synthesized. A method of preparing siRNA is not particularly limited, and a method known in the art may be used. Examples thereof include a method of directly chemically synthesizing siRNA, a method of synthesizing siRNA using in vitro transcription, a method of cleaving long double-stranded RNA synthesized by in vitro transcription using an enzyme, an expression method by intracellular transfer of a shRNA expression plasmid or viral vector, an expression method by intracellular transfer of a polymerase chain reaction (PCR)-induced siRNA expression cassette, and the like, but are not limited thereto.

In particular, the siRNA or shRNA against TSG6 of the present invention may include a sense nucleotide and an antisense nucleotide having a sequence complementary thereto, and may include a loop sequence between the sense and antisense nucleotides. As a specific example, the siRNA or shRNA against TSG6 of the present invention may include sense and antisense nucleotides of SEQ ID NOS: 3 and 4, or include sense and antisense nucleotides of SEQ ID NOS: 5 and 6. Furthermore, the siRNA or shRNA against TSG6 of the present invention may have a loop sequence of SEQ ID NO: 12 between these sequences.

As used herein, "microRNA (miRNA)" refers to a material that is naturally present in cells, and a material that is involved in the regulation of a specific gene by inducing the RNAi phenomenon. Any miRNA that can inhibit the expression or action of TSG6 of the present invention is included in the present invention without its type being limited.

In the present invention, the "antisense oligonucleotide" refers to DNA or RNA including a nucleic acid sequence complementary to that of a specific mRNA, or derivatives thereof, and may bind to a complementary sequence within mRNA to inhibit the translation of mRNA to protein. An antisense oligonucleotide sequence refers to a DNA or RNA sequence that is complementary to a TSG6 target sequence of SEQ ID NO: 1 or 2 and can bind to the sequence. Antisense oligonucleotides may have a length of 5 to 100 nucleotides, or 8 to 60 nucleotides, or 10 to 40 nucleotides, or 10 to 30 nucleotides. The antisense oligonucleotide may be synthesized in vitro by a typical method and administered in vivo, or may be administered in a form in which the antisense oligonucleotide is synthesized in vivo. Antisense oligonucleotides may be synthesized in vitro by a biological/chemical method according to a typical method in the art to which the present invention pertains. Further, a form in which an antisense oligonucleotide is synthesized in vivo may be implemented using a recombinant vector or the like which expresses the antisense oligonucleotide, and such a method may be easily carried out according to the typical methods in the art to which the present invention pertains. Therefore, the antisense oligonucleotide of the present invention may be easily designed according to a method known in the art to which the present invention pertains by referring to the base sequence of SQ ID NO: 1 or 2.

As used herein, the "aptamer" refers to a nucleic acid molecule, which is a single-stranded oligonucleotide, has a size of about 20 to 60 nucleotides, and has binding activity to a predetermined target. The aptamer has various three-dimensional structures depending on the sequence thereof, and may have high affinity for a specific material as in antigen-antibody reactions. The aptamer may inhibit the activity of a predetermined target by binding to the predetermined target. The aptamer of the present invention may be RNA, DNA, a modified nucleic acid or a mixture thereof, and may be in a linear or cyclic form. Preferably, the aptamer may serve to inhibit the expression or activity of TSG6 by binding to TSG6 mRNA. Such aptamers may be prepared from the TSG6 target sequence of SEQ ID NO: 1 or 2 by methods known to those skilled in the art.

As used herein, the term "antibody" refers to a protein molecule including an immunoglobulin molecule that is immunologically reactive with a specific antigen, and a protein molecule that acts as an antigen receptor that specifically recognizes and reacts to a specific antigen when the specific antigen enters the body. One antibody molecule consists of two heavy chains and two light chains, and each of these heavy and light chains contains a variable region and a constant region. The variable region includes three complementarity determining regions (CDRs) and four framework regions (FRs), and the complementarity determining regions may form a binding site between an antibody and an antigen to generate the binding specificity of the antibody for a specific antigen.

Antibodies that can be used in the present invention are not particularly limited as long as they suppress the activity of the TSG6 protein, and may include, for example, polyclonal antibodies, monoclonal antibodies, antibody fragments, and the like. In addition, the antibodies may include all genetically engineered antibodies such as chimeric antibodies or heterologous antibodies.

In a specific exemplary embodiment of the present invention, it was confirmed that the effect of suppressing the migration and invasiveness of cancer cells by TSG6 shRNA suppresses metastasis or invasion by suppressing the expression or action of TSG6, so that it can be seen that when a TSG6 inhibitor of the present invention is used as an anticancer agent, it has an effect of suppressing metastasis and invasion in metastatic cancer.

As used herein, the "cancer" is a disease related to the regulation of cell death, and refers to a disease caused by hyperproliferation of cells when the balance of normal cell apoptosis is broken. In some cases, such abnormal hyperproliferative cells invade surrounding tissues and organs to form a mass and destroy or deform the normal structure of the body, and such a condition is called cancer. In general, a tumor means a mass abnormally grown by autonomous overgrowth of body tissues, and may be classified into a benign tumor and a malignant tumor. The malignant tumor grows much faster than the benign tumor and may be divided into primary cancer and metastatic (invasive) cancer in which metastasis occurs while invading surrounding tissues. Such malignant tumor is typically referred to as 'cancer'.

The present invention may be a pharmaceutical composition for treating metastatic cancer, wherein the composition of the present invention has an effect of not only suppressing the proliferation of cancer, but also suppressing the metastasis of cancer cells even when cancer develops into metastatic cancer that metastasizes to other tissues. Furthermore, the active ingredient of the present invention may be a composition for treating cancer in which TSG6 overexpression occurs, or solid cancer or metastatic solid cancer in which PLK1 overexpression occurs, wherein the active ingredient suppresses the proliferation, metastasis or invasion of cancer by suppressing the expression or action of TSG6.

The cancer may be solid cancer, and specific cancer types include brain tumors, head and neck cancer, lung cancer, breast cancer, thymoma, mesothelioma, esophageal cancer, pancreatic cancer, colorectal cancer, liver cancer, gastric cancer, pancreatic cancer, biliary tract cancer, renal cancer, bladder cancer, prostate cancer, testicular cancer, germ cell tumors, ovarian cancer, cervical cancer, endometrial cancer, colon cancer, lymphoma, multiple myeloma, sarcoma, malignant melanoma and skin cancer, but the type of cancer of the present invention is not limited by the above examples.

As used herein, the "subject" refers to all animals, including humans who have cancer or have developed cancer, and cancer including liver cancer, lung cancer and the like may be alleviated or treated by administering the composition for treating the metastatic solid cancer of the present invention to an individual. The alleviation refers to all actions in which a cancer disease is ameliorated or rendered beneficial by administration of the composition according to the present invention.

As used herein, the term "treatment" refers to clinical intervention to alter the natural processes of the individual or cells to be treated, and may be carried out either during the development of a clinical pathological condition or to prevent the clinical pathological condition. The desired therapeutic effect includes preventing the occurrence or recurrence of a disease, alleviating symptoms, reducing all direct or indirect pathological consequences of the disease, preventing metastasis, reducing a disease progression rate, mitigating or temporarily alleviating a condition, or improving the prognosis. Preferably, the present invention includes all actions that ameliorate the course of cancer by administering a composition that suppresses TSG6.

An effective amount of the active ingredient of the composition for treating metastatic solid cancer of the present invention means an amount required to treat a disease. Accordingly, the effective amount of the active ingredient may be adjusted according to various factors such as the type and severity of a disease, types and contents of an active ingredient and other ingredients contained in the composition, the type of a dosage form, age, body weight, general medical conditions, gender and diet of a patient, duration and route of administration, a release rate of the composition, treatment duration, and the number of drugs simultaneously used.

Further, it is desirable to select the dosage according to the absorption rate, inactivation rate and excretion rate of the active ingredient in the body, the patient's age, sex and condition, and the severity of the disease to be treated, and the anticancer composition of the present invention, which exhibits the effect of reducing metastatic solid cancer, may be administered at a dose of 0.01 to 100 mg, preferably 0.1 to 10 mg, per kg body weight of an adult, once or several times a day.

In addition, the composition of the present invention may be parenterally administered, and is preferably administered by an infusion method of intravenous injection, intramuscular injection or intrathoracic injection when parenterally administered. To be formulated for parenteral administration, the composition may be prepared as a solution or suspension by being mixed with a stabilizer or buffer, and the preparation may be formulated in a unit dosage form in ampoules or vials.

The composition of the present invention may further include an appropriate carrier, an appropriate excipient, and an appropriate diluent, which are typically used to prepare a pharmaceutical composition. As used herein, the "pharmaceutically acceptable carrier" refers to a known pharmaceutical excipient which is useful when a pharmaceutically active compound for administration is formulated and is in fact non-toxic and insensitive under the conditions of use. The exact proportion of the excipient is determined by the solubility and chemical characteristics of the active ingredient, the selected administration route, and standard pharmaceutical practice.

A composition including a pharmaceutically acceptable carrier may be in the form of various oral or parenteral formulations. When the composition is formulated, the composition may be prepared using a commonly used diluent or excipient, such as a filler, an extender, a binder, a wetting agent, a disintegrant, and a surfactant. A solid formulation for oral administration may include a tablet, a pill, a powder, a granule, a capsule, and the like, and the solid formulation may be prepared by mixing at least one excipient, for example, starch, calcium carbonate, sucrose or lactose, gelatin, and the like with one or more compounds. Furthermore, in addition to simple excipients, lubricants such as magnesium stearate and talc may also be used. A liquid formulation for oral administration corresponds to a suspension, a liquid for internal use, an emulsion, a syrup, and the like, and the liquid formulation may include, in addition to water and liquid paraffin which are simple commonly used diluents, various excipients, for example, a wetting agent, a sweetener, a fragrance, a preservative, and the like. A preparation for parenteral administration may include an aqueous sterile solution, a non-aqueous solvent, a suspension, an emulsion, a freeze-dried preparation, and a suppository. As a non-aqueous solvent and a suspension solvent, it is possible to use propylene glycol, polyethylene glycol, a vegetable oil such as olive oil, an injectable ester such as ethyl oleate, and the like. As a base of the suppository, it is possible to use Witepsol, Macrogol, Tween 61, cacao butter, laurin fat, glycerogelatin, and the like.

Further, the composition of the present invention may have any one formulation selected from the group consisting of a tablet, a pill, a powder, a granule, a capsule, a suspension, a liquid for internal use, an emulsion, a syrup, a sterilized aqueous solution, a non-aqueous solvent, a suspension, an emulsion, a freeze-dried preparation, and a suppository, but the formulation is not limited thereto. In addition, the composition may be preferably formulated according to each disease or according to the ingredient using an appropriate method in the art, a method described in the Remington's Pharmaceutical Science, Mack Publishing Company, Easton PA, or the like.

The present invention also provides a method for treating metastatic solid cancer, the method including administering a therapeutically effective amount of a TSG6 inhibitor that targets a nucleotide sequence of SEQ ID NO: 1 or 2 to a subject in need thereof.

The subject may be a human or an animal other than a human, for example, a non-human animal such as a cow, a monkey, a bird, a cat, a mouse, a rat, a hamster, a pig, a dog, a rabbit, a sheep, and a horse.

In the treatment method of the present invention, the formulation, administration method, and the like of the composition are as described above.

Hereinafter, the present invention will be described in more detail with reference to the following Examples. However, the following Examples are only for exemplifying the present invention, and the scope of the present invention is not limited to the following Examples.

EXAMPLES

Example 1: Analysis of TSG6 Expression in PLK1 Wild Type and Active Form-Expressing Cells with Metastatic Potential Lung cancer cells A549 expressing the PLK1 wild type or active form protein were obtained by being allowed to pass through Matrigel so as to have invasiveness, which is one of the metastatic abilities, and a microarray analysis was performed by obtaining mRNA of non-invasive cells and invasive cells.

Specifically, Matrigel was completely dissolved at 4° C. for 16 to 20 hours, and then diluted with cold serum-free MEM (4° C.) to 1 mg/mL. 1 mL of the Matrigel mixture (1 mg/mL) was put into an 8.0 mm 6-well insert and solidified in an incubator at 37° C. for 12 to 20 hours. A549 lung cancer cells expressing PLK1 wild type (WT) and active form PLK1 (TD) proteins were diluted in serum-free MEM (36° C.) to a cell number of $2 \times 10^5$ cells/well and dispensed into the solidified Matrigel insert and dispensed into the insert. 0.5 mL/well of warm MEM (including 10% FBS) at 36° C. was added thereto. Thereafter, the media were exchanged once every 3 days and the degree of invasion was observed, and on day 5 when sufficient invasion of cancer cells was observed, the medium was removed and washed with 1×PBS, and then cells inside the insert were removed by scraping with a cotton swab such that any remnants of cells and Matrigel inside the insert did not remain. To detach invasive cells from the outer surface of the insert, 3 mL of trypsin was added to a 6-well plate, and the insert was placed in an incubator at 36° C. for 5 minutes. After 5 minutes, the cells attached to the insert were detached with a pipette, and even the invasive cells that had fallen into the 6-well plate were collected and centrifuged at 1000 rpm for 5 minutes to collect the cells. After the cells were fully lysed by adding TRIzol to the collected cells, chloroform was added thereto and the resulting mixture was allowed to react at room temperature for 10 minutes. The organic layer was removed by centrifugation at 14000 rpm and 4° C. for 10 minutes, and the aqueous layer was transferred to a new 1.5 mL-tube. After the supernatant was removed by adding isopropanol and performing centrifugation at 14000 rpm and 4° C. for 10 minutes, the sedimented RNA was washed using 75% ethanol dissolved in DEPC. After centrifugation was performed at 14000 rpm and 4° C. for 10 minutes and the supernatant was removed, the RNA was dried on a clean bench. The dried RNA was dissolved in sterile distilled water and stored. The obtained RNA was given to a microarray analysis team that was commissioned to perform microarray analysis.

The top 5 genes most frequently expressed by active form PLK1-expressing cells having invasiveness were confirmed using gene expression data obtained by the microarray, and an increase in the expression of TNFAIP6 (gene name of TSG6 protein) in active form PLK1-expressing cells was observed using real-time PCR instead of the microchip.

Figure 1:
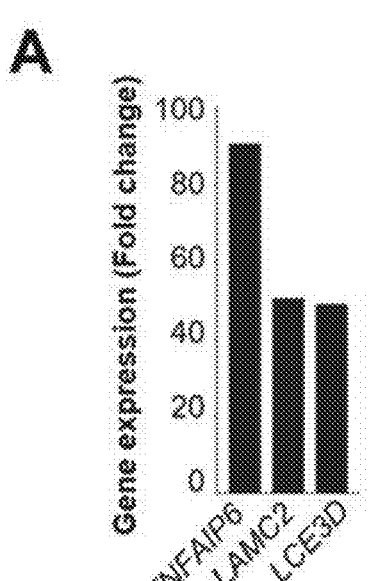
FIG. 1 shows the results of analyzing an increase in TSG6 expression in invasive cancer cells expressing the wild type or active form of PLK1 according to embodiments of the present invention, A is a graph listing genes whose expressions are increased in cancer cells expressing active form PLK1 in order based on the results of microarray analysis using invasive cancer cells expressing the wild type or active form of PLK1, and B is a graph of mRNA analysis results in wild type or active form PLK1 using real-time polymerase chain reaction (real-time PCR). As a positive control, TGF-β was treated, which is known to induce epithelial-mesenchymal transition.
Figure 1:
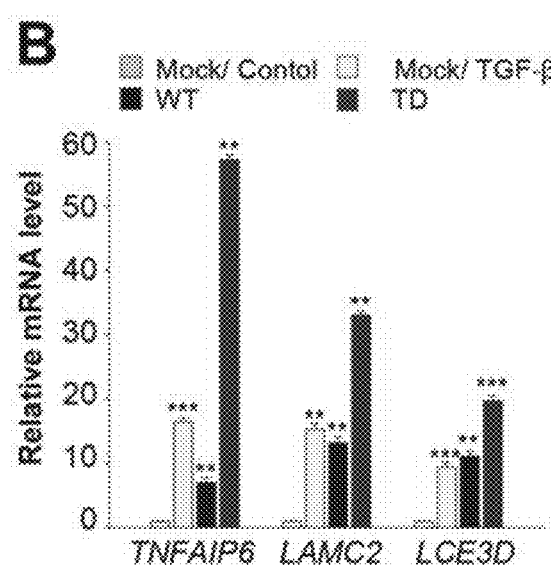

From the results of the microarray in FIG. 1A, TNFAIP6 gene expression was increased in lung cancer cells A549 expressing the PLK1 wild type or active form protein having invasiveness, and particularly in invasive cells expressing active form PLK1, it was analyzed that the expression was highest with 6.6-fold higher expression than the control. It was observed that TNFAIP6 (TSG6) was also increased in PLK1 active form-expressing cells in the real-time PCR results in FIG. 1B, and TNFAIP6 (TSG6) was also increased in the TGF-β treatment group, which induces epithelial-mesenchymal transition.

Therefore, it could be seen that TSG6 may be a therapeutic target in metastatic cancer because the expression of the PLK1 active form, which is known to induce metastasis, and an anti-inflammatory factor TSG6 are increased in the TGF-β-treated environment.

Example 2: Evaluation of Metastasis Effect According to Expression of TSG6

Through the above results, it was attempted to analyze the effect of TSG6 on epithelial-mesenchymal transition by treating lung cancer cells with TSG6 to observe the changes on the expression of TSG6, PLK1 and active form PLK1 in cells and the expression of epithelial-mesenchymal transition markers and cancer metastasis-associated factors. Furthermore, in order to observe the effect on cancer migration and invasiveness, a cell migration assay and a cell invasion assay were each performed to analyze the effect of TSG6 on cancer metastasis.

First, the expression pattern of genes included in immune evasion, a cancer stem cell (CSC) and a mesenchymal marker, in which the expression of TNFAIP6 is involved in the metastasis in general tissues and cancer tissues according to stages of lung cancer patients, was analyzed using Morpheus program software. Specifically, classification was made into general tissues, Stage 1 cancer tissues, and Stage 2-4 cancer tissues where metastasis of lung cancer patients may be induced using TCGA big data with Morpheus (software(dot)broadinstitute(dot)org/morpheus/). Next, genes included in immune evasion; genes included in CD274, CD28, CD80, CD86, CD8A, CD8B, CTLA4, CXCR4, PDCD1, PDCD1LG2 and cancer stem cells (CSCs); genes corresponding to CD44, THY1, PROM1, ALDH1A3, PLAUR, BMI1, CD33, ABCG2, and mesenchymal markers; VIM, CDH2, ZEB1, ZEB2, SNAI1, SNAI2, TWIST1, TWIST2, FN1, MMP2, MMP3, MMP9, and PLK1 were searched for and listed, summarized in the expression order of TNFAIP6, and then expressed as a heat map.

As illustrated in FIG. 2A, Stage 2-4 cancer tissue with the potential of metastasis being induced, also had high expression patterns of genes included in immune evasion, cancer stem cells (CSCs) and mesenchymal markers involved in metastasis as the expression of TNFAIP6 was high, compared to general tissues, so that the metastatic potential according to the increase in TNFAIP6 expression could be observed.

Next, in order to observe the epithelial-mesenchymal transition by TSG6 treatment in cellular experiments, lung cancer cells A549 were cultured to $5\times10^4$ cells/mL, and then treated with 200 ng/ml of LTSG6 for 2 hours the next day and the cells were collected. The collected cells were treated with 100 µl of a lysing solution (0.5% Triton X-100, 20 mM Tris, pH 7.5, 2 mM MgCl₂, 1 mM DTT, 1 mM EGTA, 50 mM beta-glycerophosphate, 25 mM NaF, 1 mM Na₃VO₄, 2 µg/mL leupeptin, 2 µg/mL pepstatin A, 100 µg/mL PMSF, and 1 µg/mL antipain), and then proteins were quantified. After electrophoresis of the quantified proteins through SDS-PAGE, immunoblotting was performed using each epithelial-mesenchymal transition marker antibody to confirm the expression of factors associated with the epithelial-mesenchymal transition process at the protein expression level.

As illustrated in FIG. 2B, it was observed that intracellular TSG6 expression was increased by TSG6 treatment, and it was observed that the expression of active form PLK1 was also increased compared to the control. Further, by TSG6 treatment, an increase in N-cadherin, which is a mesenchymal transition marker, and a decrease in E-cadherin, which is an epithelial marker, were observed, and an increase in expression of phosphorylated Smad2 (S465/467), which is a main protein of the TGF-β signaling pathway, was observed.

Next, factors associated with epithelial-mesenchymal transition markers after TSG6 treatment were observed at the mRNA level in order to evaluate the increase in epithelial-mesenchymal transition according to the treatment of TSG6. Specifically, A549 cells were cultured to $5\times10^4$ cells/mL and then treated with 200 ng/mL of LTSG6 for 2 hours the next day and the cells were collected. Real-time PCR was performed by isolating mRNA from the collected cells and synthesizing cDNA, and by observing epithelial-mesenchymal transition markers and associated factors at the mRNA level, it was confirmed that TSG6 treatment increases the epithelial-mesenchymal transition process.

As illustrated in FIG. 2C, TSG6-treated cells had an increase in mesenchymal transition markers such as CDH2 and a decrease in an epithelial marker CDH1 compared to control cells. In addition, it was observed that the expression of TGFB1 and PLK1 was also increased by TSG6 treatment.

Furthermore, an effect in which TSG6 suppresses the migration of cells was demonstrated in a metastatic environment where active form PLK1 was expressed using a cell migration assay. Specifically, control cells (Mock) and cells expressing active form PLK1 (PLK1-TD) were diluted in serum-free MEM (36° C.) to a cell number of $5\times10^4$ cells/well and seeded on a 24-well insert. 0.5 mL/well of MEM (10% FBS) supplemented with serum was dispensed into the 24-well plate outside the insert. Cells were treated with TSG6 by putting an experimental group treated with 200 ng/ml of TSG6 into MEM containing serum. After 48 hours of TSG6 treatment, migrated cells were immobilized by dispensing 500 µl of 4% para-formaldehyde, washed three times with 1×PBS, and stained with a 0.05% crystal-violet solution for 5 minutes. After 5 minutes, the cells were washed five times with 1×PBS and the degree of staining was measured at a wavelength of 590 nm. When the absorbance of the control is defined as 1, the relative absorbance in each experimental group was calculated and graphed.

As illustrated in FIG. 2D, TSG6-treated cells showed an increase in cell migration compared to control cells (Mock), and active form PLK1 (PLK1-TD) in which active form PLK1 is expressed showed at least a two-fold increase in the migration of cells by TSG6 treatment.

Next, an effect in which TSG6 treatment further increases the migration of cells in a metastatic environment induced by TGF-β treatment was demonstrated using a cell migration assay. Specifically, lung cancer cells A549 were diluted in serum-free medium, $5\times10^4$ cells were dispensed into an 8.0 µm 24-well insert (BD Biosciences, NJ, USA), and a medium containing 10% serum (MEM) was dispensed into a 24-well plate, and then the insert was put thereinto. Each experimental group treated with 2.5 ng/ml of TGF-β or 200 ng/ml of TSG6 and the experimental group treated with a mixture of both TGF-β and TSG6 were put into serum-containing media (MEM) and the cells were treated with the media. After 48 hours of TSG6 or TGF-β treatment, migrated cells were immobilized by dispensing 500 µl of 4% para-formaldehyde, washed three times with 1×PBS, and stained with a 0.05% crystal-violet solution for 5 minutes. After 5 minutes, the cells were washed five times with 1×PBS and the degree of staining was measured at a wavelength of 590 nm. When the absorbance of the control is defined as 1, the relative absorbance in each experimental group was calculated and graphed.

As illustrated in FIG. 2E, it was observed that the cell migration of TSG6-treated cells in a TGF-β-treated metastatic environment was further increased upon TSG6 treatment.

Figure 2:
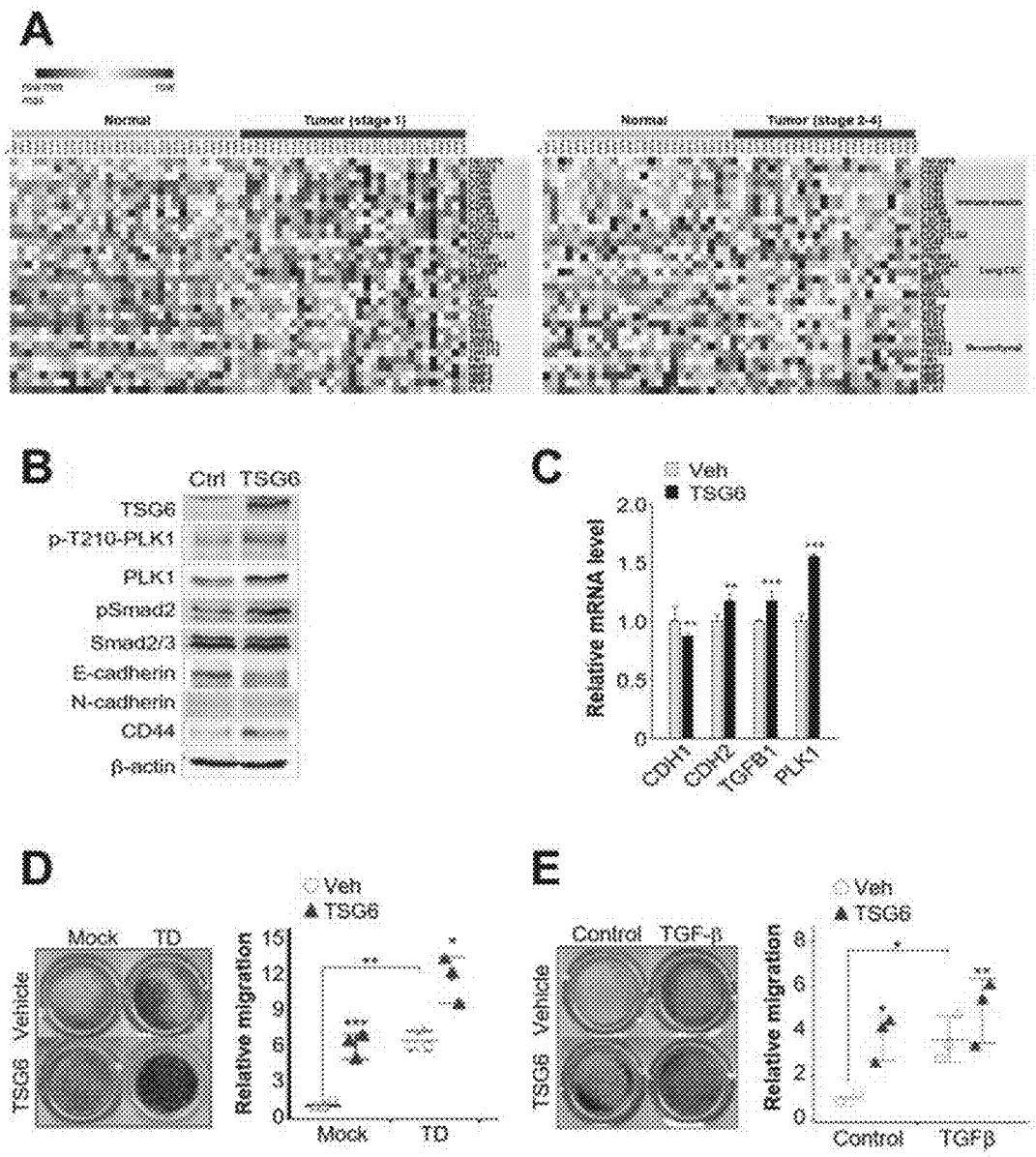
FIG. 2 shows the results of observing protein expression changes and mRNA expression changes of TSG6, a PLK1 active form (TD-PLK1), PLK1, phosphorylated Smad2, Smad2/3, epithelial-mesenchymal transition markers (E-cadherin, N-cadherin), and CD44 when lung cancer cells are treated with TSG6. In addition.

Combining the results of FIG. 2, it could be seen that an increase in intracellular TSG6 due to TSG6 treatment increased the expression of factors involved in the epithelial-mesenchymal transition of cells. Further, it was demonstrated that TSG6 treatment further increased the migration of cells even in a metastatic environment where active form PLK1 was expressed and in a metastatic environment by TGF-β treatment.

Example 3: Evaluation of Cancer Cell-Killing Effect of TSG6 shRNA and Evaluation of Effect of TSG6 shRNA on Suppression of Epithelial-Mesenchymal Transition in Metastatic Environment by PLK1 Active Form Expression In order to confirm the effect of TSG6 on the suppression of mRNA expression, shRNA and a lentivirus containing the shRNA were prepared. Specifically, in order to suppress the mRNA expression of TSG6, primers were prepared so as to construct shRNAs targeting nucleotide sequences at positions 530-550 or 693-713 of the human TSG6 mRNA (Human TNFAIP6 mRNA [NM_007115.4]) sequence. By using 5'-CAAATGAGTACGAAGATAACC-3'(SEQ ID NO: 3) as the sense region that targets the 530-550 nucleotide sequence (SEQ ID NO: 1) and the 5'-GGT-TATCTTCGTACTCATTTG-3'(SEQ ID NO: 4) region as the antisense region, a pLKO-puro.1-TNFAIP6 plasmid was constructed using a PLKO-puro.1 vector based on the sense and antisense regions. 5'-CCGGCAAATGAGTACGAA-GATAACCCTCGAGGGTTATCTTCGTACTCATT TGT-TTTTG-3'(SEQ ID NO: 8) was used as a forward primer, and 5'-AATTCAAAAACAAATGAGTACGAAGATAAC-CCTCGAGGGTTATCTTCGT ACTC-ATTTG-3'(SEQ ID NO: 9) was used as a reverse primer.

By using 5'-GGGAAGATACTGTGGAGATGA-3'(SEQ ID NO: 5) as the sense region of shRNA that targets the 693-713 nucleotide sequence (SEQ ID NO: 2) and the 5'-TCATCTCCACAGTATCTTCCC-3'(SEQ ID NO: 6) region as the antisense region, a pLKO-puro.1-TNFAIP6 plasmid was constructed using a PLKO-puro.1 vector based on the sense and antisense regions. 5'-CCGGGGGAAGA-TACTGTGGAGATGACTCGAGTCATCTCCACAGTAT-CTTC CCTTTTTG-3'(SEQ ID NO: 10) was used as a forward primer, and 5'-AATTCAAAAAGGGAAGA-TACTGTGGAGATGACTCGAGTCATCTCCACAG TAT-CTTCCC-3'(SEQ ID NO: 11) was used as a reverse primer.

The loop sequence is 5'-CTCGAG-3'(SEQ ID NO: 12), and shRNA was constructed in a form included in the primer. After the shRNA was expressed together with pHR'-CMV-VSVG and pHR'-CMV-deltaR8.2 through HEK293 cell transfection, the culture medium of cells was collected to produce a lentivirus. The lentivirus was concentrated using a centrifuge. In order to confirm virus expression, after A549 cells were cultured to $5 \times 10^4$ cells/mL, the next day, cancer cells were infected by adding a lentivirus at 20 mL/well to an infection buffer (10 mM HEPES (Sigma-Aldrich, USA), 1 mg/mL polybrene (Sigma-Aldrich, MO, USA)). After 24 hours, surviving infected cells were selected by treating the cells with puromycin (Sigma-Aldrich, MO, USA) for 48 hours, and by taking the RNA of the selected cells, it was observed by real-time PCR that the expression of TSG6 was suppressed.

As illustrated in FIG. 3A, shTNFAIP6-infected lung cancer cells A549 showed a decrease in TNFAIP6 mRNA expression compared to control shRNA (shCtrl)-infected cells, indicating that the expression of TNFAIP6 was suppressed.

Next, cell death was evaluated when the expression of TSG6 was suppressed in cancer cells. Specifically, control cells (Mock) and cells expressing active form PLK1 (PLK1-TD) were cultured to $5 \times 10^4$ cells/mL and infected with a control virus (shCtrl) or shTNFAIP6, and then treated with puromycin for 48 hours to select and collect live cells that survived. The collected cells were treated with 100 µl of a lysing solution (0.5% Triton X-100, 20 mM Tris, pH 7.5, 2 mM $MgCl_2$, 1 mM DTT, 1 mM EGTA, 50 mM beta-glycerophosphate, 25 mM NaF, 1 mM $Na_3VO_4$, 2 µg/mL leupeptin, 2 µg/mL pepstatin A, 100 µg/mL PMSF, and 1 µg/mL antipain), and then proteins were quantified. After electrophoresis of the quantified proteins through SDS-PAGE, apoptosis was confirmed using cleaved capase-3 and cleaved PARP antibodies capable of confirming cell death.

As illustrated in FIG. 3B, cleaved capase-3 and cleaved PARP were observed in control cells when the expression of TSG6 was suppressed, and these results show that suppression of TSG6 expression can induce cancer cell death. In addition, these results show that when the expression of TSG6 is suppressed even in cancer cells expressing active form PLK1 (PLK1-TD), which induces metastasis, cleaved capase-3 and cleaved PARP are detected, and cell death can be induced.

Next, in order to evaluate a reduction in epithelial-mesenchymal transition by suppressing TSG6 expression, TSG6 shRNA was used in a metastatic environment where active form PLK1 was expressed to suppress the expression of TSG6 expression and observe epithelial-mesenchymal transition markers at the protein level.

Specifically, control cells (Mock) and cells expressing active form PLK1 (PLK1-TD) were cultured to $5 \times 10^4$ cells/mL and infected with a control virus (shCtrl) or shTN-FAIP6, and then treated with puromycin for 48 hours to select and collect live cells that survived. The collected cells were treated with 100 µl of a lysing solution (0.5% Triton X-100, 20 mM Tris, pH 7.5, 2 mM $MgCl_2$, 1 mM DTT, 1 mM EGTA, 50 mM beta-glycerophosphate, 25 mM NaF, 1 mM $Na_3VO_4$, 2 µg/mL leupeptin, 2 µg/mL pepstatin A, 100

µg/mL PMSF, and 1 µg/mL antipain), and then proteins were quantified. After electrophoresis of the quantified proteins through SDS-PAGE, immunoblotting was performed using epithelial-mesenchymal transition marker antibodies to confirm a reduction in the epithelial-mesenchymal transition process. Furthermore, real-time PCR was performed by isolating mRNA from the collected cells and synthesizing cDNA, and by observing epithelial-mesenchymal transition markers at the mRNA level, it was confirmed that TSG6 shRNA reduces the epithelial-mesenchymal transition process in a metastatic environment induced by active form PLK1.

As illustrated in FIG. 3C, in cells expressing active form PLK1 (PLK1-TD), mesenchymal transition markers such as Vimentin, Snail, and Slug including N-cadherin were increased, and an epithelial marker E-cadherin was decreased compared to the control cells (Mock). Further, the expression of Smad2/3 and p-Smad2 (S465/467), which are major proteins in the TGF-β signaling pathway known as the main pathway of epithelial-mesenchymal transition, was increased during the cancer metastasis process, and these results imply that cells expressing active form PLK1 (PLK1-TD) induce an epithelial-mesenchymal transition environment through the TGF-β signaling pathway. In such an environment, it was observed that when the expression of TSG6 was suppressed using shTNFAIP6, the expression of p-Smad2 (S4 65/467), a major protein in the TGF-β signaling pathway, was decreased, and mesenchymal transition markers such as Vimentin, Snail, and Slug including N-cadherin were increased. In the results not only at the protein level, but also at the mRNA level shown in FIG. 3D, it was observed that in cells expressing active form PLK1 (PLK1-TD), CDH2, which is a mesenchymal transition marker, was increased, and CDH1, which is an epithelial marker, was decreased compared to control cells (Mock). Therefore, the present invention demonstrated that the suppression of TSG6 expression reduces active form p-Smad2 (S465/467) and inhibits epithelial-mesenchymal transition in cancer metastasis caused by TGF-β signaling pathway activity.

In addition, in order to demonstrate the effect of TSG6 shRNA on suppressing cell migration using an insert in a metastatic environment where active PLK1 was expressed, control cells (Mock) and cells expressing active form PLK1 (PLK1-TD) were diluted in serum-free MEM (36° C.) to a cell number of $5 \times 10^4$ cells/well and seeded on a 24-well insert. 0.5 mL/well of MEM (containing 10% FBS) was dispensed into the 24 well plate outside the insert, and after 24 hours, the cells were infected with control shRNA (shCtrl) or TSG6 shRNA (shTNFAIP6) virus. The next day, the cells were treated with puromycin for 48 hours, and 4 days after virus infection, the cells were treated with 500 µl of 4% para-formaldehyde, washed three times with 1×PBS, and stained with a 0.05% crystal-violet solution for 5 minutes. After 5 minutes, the cells were washed five times with 1×PBS and the degree of staining was measured at a wavelength of 590 nm. When the absorbance of the control is defined as 1, the relative absorbance in each experimental group was calculated and graphed.

As illustrated in FIG. 3E, cells expressing active form PLK1 (PLK1-TD) treated with the control virus (shCtrl) showed an increase in cell migration compared to the control cells (Mock), and suppression of TSG6 expression by infection with shTNFAIP6 reduced cell migration despite the expression of active form PLK1.

Next, the effect of TSG6 shRNA on suppressing cell invasiveness was demonstrated using Matrigel in a metastatic environment where active form PLK1 was expressed.

For this purpose, Matrigel was completely dissolved at 4° C. for 16 to 20 hours, and then diluted with cold serum-free MEM (4° C.) to 1 mg/mL. 1 mL of the Matrigel mixture (1 mg/mL) was put into an 8.0 mm 24-well insert and solidified in an incubator at 37° ° C. for 12 to 20 hours. Each of control cells (Mock) or active form PLK1-expressing cells (PLK1-TD) were diluted in serum-free MEM (36° C.) to a cell number of $2\times10^5$ cells/well and dispensed into the solidified Matrigel insert and dispensed into the insert. 0.5 mL/well of warm MEM (including 10% FBS) at 36° ° C. was added thereto. Thereafter, the media were exchanged once every 3 days and the degree of invasion was observed, and on day 5 when sufficient invasion of cancer cells was observed, the medium was removed and washed with 1×PBS, and then cells inside the insert were removed by scraping with a cotton swab and washing with 1×PBS, such that any remnants of cells and Matrigel inside the insert did not remain. 500 µl of 4% para-formaldehyde was added to 24-wells on the outer surface of the insert, the wells were incubated at room temperature for 5 minutes, and then washed three times with 1×PBS after 5 minutes, and stained with a 0.05% crystal-violet solution for 5 minutes. After 5 minutes, the cells were washed five times with 1×PBS and the degree of staining was measured at a wavelength of 590 nm. When the absorbance of the control is defined as 1, the relative absorbance in each experimental group was calculated and graphed.

As illustrated in FIG. 3F, cells expressing active form PLK1 (PLK1-TD) treated with the control virus (shCtrl) showed an increase in cell invasiveness compared to the control cells (Mock), and suppression of TSG6 expression by infection with shTNFAIP6 reduced cell invasiveness despite the expression of active form PLK1.

When the above results are taken together, it was demonstrated that cells expressing active form PLK1 (PLK1-TD) have a metastatic environment that not only increases epithelial-mesenchymal transition, but also increases cell migration and invasiveness, and suppression of TSG6 expression using TSG6 shRNA in such a metastatic environment reduced not only epithelial-mesenchymal transition, but also cell migration and invasiveness.

Example 4: Evaluation of Effect of TSG6 shRNA on Suppressing Epithelial-Mesenchymal Transition in Metastatic Environment by TGF-β Treatment When the expression of TSG6 was suppressed using TSG6 shRNA in a cancer metastatic environment induced by TGF-β treatment, changes in mRNA expression of epithelial-mesenchymal transition markers and associated factors were observed by polymerase chain reaction, and cell migration experiments and cell invasiveness experiments were performed to observe the effects on cancer migration and invasiveness, respectively.

Specifically, after the TSG6 shRNA (shTNFAIP6) constructed in Example 2 was expressed together with pHR'-CMV-VSVG and pHR'-CMV-deltaR8.2 through HEK293 cell transfection, the culture medium of cells was collected to produce a lentivirus. The lentivirus was concentrated using a centrifuge. After A549 cells, which are lung cancer cells, were infected with the produced virus, an experiment was performed to examine the effect of TSG6 shRNA on the metastasis of lung cancer cells induced by TGF-β treatment. The cells were divided into a shCtrl control and a shTN FAIP6 experimental group (TSG6 shRNA treatment group) according to the treatment of shRNA, and 20 µl of viral TSG6 shRNA expressed using plKO-puro.1-TNFAIP6, which was constructed to suppress the expression of TSG6 mRNA in lung cancer cell A549, was taken and mixed with an infection buffer (10 mM HEPES, 1 µg/mL polybrene), and cells were treated with the resulting mixture. After 24 hours, the cells were treated with 2 µg/mL of puromycin for 48 hours to select only cells infected with TSG6 shRNA, thereby constructing a cell line that suppresses TSG6 expression. After RNA was isolated under a condition that induces cancer metastasis by treating the constructed cell line that suppresses TSG6 with 2.5 ng/mL TGF-β for 48 hours, the expression of TNIFAIP6 and the expression of CDH1, CDH2, PLK1, TGFB1, and CD44, which are factors associated with epithelial-mesenchymal transition, were observed by real-time PCR.

As illustrated in FIG. 4A, TSG6 shRNA(shTNFAIP6)-infected lung cancer A549 showed a decrease in TNFAIP6 mRNA expression compared to control shRNA (shCtrl)-infected cells, this suppressed the expression of TNFAIP6, and it was observed that the expression of TNFAIP6 was suppressed even under the condition of treatment with TGF-β that induces a cancer metastatic environment. It was observed that the decrease in the expression of CDH1 mRNA, which is an epithelial marker, by TGF-β treatment was suppressed by the suppression of TNFAIP6 expression by shTNFAIP6 treatment, and the increase in the expression of PLK1, TGF-β and CD44 including CDH2, which is a mesenchymal transition marker by TGF-β treatment was also suppressed by the suppression of TNFAIP6 expression.

Next, the effect of TSG6 expression suppression on cell migration was confirmed through cell migration experiments in a TGF-β-treated metastatic environment. For this purpose, lung cancer cells A549 were diluted in serum-free medium, $5\times10^4$ cells were dispensed into an 8.0 µm 24-well insert (BD Biosciences, NJ, USA), and a medium containing 10% serum (MEM) was dispensed into a 24-well plate], and then the insert was put thereinto. After 24 hours, the cells were infected with control shRNA (shCtrl) or TSG6 shRNA (shTN FAIP6) viruses. The next day, the cells were treated with 2 µg/mL of puromycin for 48 hours and then treated with 2.5 ng/ml of LTGF-β for 48 hours. After 48 hours of TGF-β treatment, migrated cells were immobilized by dispensing 500 µl of 4% para-formaldehyde, washed three times with 1×PBS, and stained with a 0.05% crystal-violet solution for 5 minutes. After 5 minutes, the cells were washed five times with 1×PBS and the degree of staining was measured at a wavelength of 590 nm. When the absorbance of the control is defined as 1, the relative absorbance in each experimental group was calculated and graphed.

As illustrated in FIG. 4B, it was observed that cells infected with shTNFAIP6 to suppress the expression of TSG6 had suppressed cell migration compared to cells treated with a control virus (shCtrl), and the suppression of TSG6 expression by shTNFAIP6 suppressed cell migration even in a metastatic environment by TGF-β treatment.

Next, the effect of TSG6 shRNA on suppressing cell invasiveness was confirmed through cell invasiveness experiments in a metastatic environment by TGF-β treatment. For this purpose, Matrigel was completely dissolved at 4° C. for 16 to 20 hours, and then diluted in cold MEM containing no serum (4° C.) to 1 mg/mL. 150 µl of the Matrigel mixture was dispensed into an 8.0 µm 24-cell insert and solidified in an incubator at 37° C. for 12 to 20 hours. Lung cancer cells A549 were diluted in serum-free medium to a cell number of $2\times10^5$ cells/well and dispensed on the solidified Matrigel. 0.5 mL/well of warm MEM (10% FBS) containing serum at 36° C. was added thereto. After 24 hours, the cells were infected with control shRNA (shCtrl) or TSG6 shRNA (shTN FAIP6) viruses. The next day, the cells were treated with 2 μg/mL of puromycin for 48 hours and then treated with 2.5 ng/ml of LTGF-β for 48 hours. Thereafter, the media were exchanged once every 3 days and the degree of invasion was observed, and on day 5 when sufficient invasion of cancer cells was observed, the medium was removed and washed with 1×PBS, and then cells inside the insert were removed by scraping with a cotton swab and washing with 1×PBS, such that any remnants of cells and Matrigel inside the insert did not remain. 500 μl of 4% para-formaldehyde was added to 24-well plates on the outer surface of the insert, cells that had invaded the Matrigel were incubated at room temperature for 5 minutes, and then washed three times with 1×PBS after 5 minutes, and stained with a 0.05% crystal-violet solution for 5 minutes. After 5 minutes, the cells were washed five times with 1×PBS and the degree of staining was measured at a wavelength of 590 nm. When the absorbance of the control is defined as 1, the relative absorbance in each experimental group was calculated and graphed.

As illustrated in FIG. 4C, it was observed that cells infected with shTNFAIP6 to suppress the expression of TSG6 had suppressed cell invasiveness compared to cells treated with a control virus (shCtrl), and the suppression of TSG6 expression by shTNFAIP6 suppressed cell invasiveness even in a metastatic environment by TGF-β treatment.

When the results of FIG. 4 are taken together, it was demonstrated that the suppression of TSG6 expression by shTNFAIP6 not only suppresses the expression of factors involved in cell epithelial-mesenchymal transition, but also reduces cell migration and invasiveness, and the suppression of TSG6 expression by shTNFAIP6 even in a metastatic environment by TGF-β treatment suppresses the expression of factors associated with epithelial-mesenchymal transition, and also reduces cell migration and invasiveness.

The present invention can be usefully used in the field of treatment of metastatic cancer.

---

What is claimed is:

1. A composition for treating metastatic solid cancer, comprising a tumor necrosis factor-inducible gene 6 protein (TSG6) inhibitor that targets the base sequence of SEQ ID NO: 1 or 2, wherein the TSG6 inhibitor is selected from the group consisting of:

shRNA comprising the base sequences of SEQ ID Nos. 3 and 4, and shRNA comprising the base sequences of SEQ ID Nos. 5 and 6.

2. A method for treating metastatic solid cancer, the method comprising: administering a therapeutically effective amount of a tumor necrosis factor-inducible gene 6 protein (TSG6) inhibitor that targets the base sequence of SEQ ID NO: 1 or 2 to a subject in need thereof.

3. The method of claim 2, wherein the TSG6 inhibitor is any one of siRNA, shRNA, miRNA, an antisense oligonucleotide or an aptamer, which specifically binds to the base sequence of SEQ ID NO: 1 or 2.

4. The method of claim 2, wherein the TSG6 inhibitor is shRNA comprising the base sequences of SEQ ID NOS: 3 and 4.

5. The method of claim 2, wherein the TSG6 inhibitor is shRNA comprising the base sequences of SEQ ID NOS: 5 and 6.

6. The method of claim 2, wherein the solid cancer is selected from the group consisting of brain tumors, head and neck cancer, lung cancer, breast cancer, thymoma, mesothelioma, esophageal cancer, pancreatic cancer, colorectal cancer, liver cancer, gastric cancer, pancreatic cancer, biliary tract cancer, renal cancer, bladder cancer, prostate cancer, testicular cancer, germ cell tumors, ovarian cancer, cervical cancer, endometrial cancer, colon cancer, lymphoma, multiple myeloma, sarcoma, malignant melanoma and skin cancer.

\* \* \* \* \*

SEQUENCE LISTING

<160> NUMBER OF SEQ ID NOS: 12

<210> SEQ ID NO 1
<211> LENGTH: 21
<212> TYPE: DNA
<213> ORGANISM: Artificial Sequence
<220> FEATURE:
<223> OTHER INFORMATION: TSG6 530-550 nt

<400> SEQUENCE: 1
caaatgagta cgaagataac c                                        21

<210> SEQ ID NO 2
<211> LENGTH: 21
<212> TYPE: DNA
<213> ORGANISM: Artificial Sequence
<220> FEATURE:
<223> OTHER INFORMATION: TSG6 693-713 nt

<400> SEQUENCE: 2
gggaagatac tgtggagatg a                                        21

<210> SEQ ID NO 3
<211> LENGTH: 21
<212> TYPE: DNA
<213> ORGANISM: Artificial Sequence
<220> FEATURE:
<223> OTHER INFORMATION: TSG6 shRNA sense nucleotide

<400> SEQUENCE: 3
caaatgagta cgaagataac c                                        21

<210> SEQ ID NO 4
<211> LENGTH: 21
<212> TYPE: DNA
<213> ORGANISM: Artificial Sequence
<220> FEATURE:
<223> OTHER INFORMATION: TSG6 shRNA antisense nucleotide

<400> SEQUENCE: 4
ggttatcttc gtactcattt g                                        21

<210> SEQ ID NO 5
<211> LENGTH: 21

-continued

```
<212> TYPE: DNA
<213> ORGANISM: Artificial Sequence
<220> FEATURE:
<223> OTHER INFORMATION: TSG6 shRNA sense nucleotide

<400> SEQUENCE: 5
gggaagatac tgtggagatg a                                                 21

<210> SEQ ID NO 6
<211> LENGTH: 21
<212> TYPE: DNA
<213> ORGANISM: Artificial Sequence
<220> FEATURE:
<223> OTHER INFORMATION: TSG6 shRNA antisense nucleotide

<400> SEQUENCE: 6
tcatctccac agtatcttcc c                                                 21

<210> SEQ ID NO 7
<211> LENGTH: 1422
<212> TYPE: DNA
<213> ORGANISM: Homo sapiens

<400> SEQUENCE: 7
agtcacattt cagccactgc tctgagaatt tgtgagcagc ccctaacagg ctgttacttc       60
actacaactg acgatatgat catcttaatt tacttatttc tcttgctatg ggaagacact      120
caaggatggg gattcaagga tggaattttt cataactcca tatggcttga acgagcagcc      180
ggtgtgtacc acagagaagc acggtctggc aaatacaagc tcacctacgc agaagctaag      240
gcggtgtgtg aatttgaagg cggccatctc gcaacttaca agcagctaga ggcagccaga      300
aaaattggat ttcatgtctg tgctgctgga tggatggcta agggcagagt ggatacccc       360 attgtgaagc cagggcccaa ctgtggattt ggaaaaactg gcattattga ttatggaatc      420
cgtctcaata ggagtgaaag atgggatgcc tattgctaca acccacacgc aaaggagtgt      480
ggtggcgtct ttacagatcc aaagcaaatt tttaaatctc caggcttccc aaatgagtac      540
gaagataacc aaatctgcta ctggcacatt agactcaagt atggtcagcg tattcacctg      600
agttttttag attttgacct tgaagatgac ccaggttgct tggctgatta tgttgaaata      660
tatgacagtt acgatgatgt ccatggcttt gtgggaagat actgtggaga tgagcttcca      720
gatgacatca tcagtacagg aaatgtcatg accttgaagt ttctaagtga tgcttcagtg      780
acagctggag gtttccaaat caaatatgtt gcaatggatc ctgtatccaa atccagtcaa      840
ggaaaaaata caagtactac ttctactgga aataaaaact ttttagctgg aagatttagc      900
cacttataaa aaaaaaaaaa aggatgatca aaacacacag tgtttatgtt ggaatctttt      960
ggaactcctt tgatctcact gttattatta acatttattt attattttttc taaatgtgaa     1020 agcaatacat aatttaggga aaattggaaa atataggaaa ctttaaacga gaaaatgaaa     1080
cctctcataa tcccactgca tagaaataac aagcgttaac attttcatat ttttttctt      1140 cagtcatttt tctatttgtg gtatatgtat atatgtacct atatgtattt gcatttgaaa     1200
ttttggaatc ctgctctatg tacagttttg tattatactt tttaaatctt gaactttata     1260
aacattttct gaaatcattg attattctac aaaaacatga ttttaaacag ctgtaaaata     1320
ttctatgata tgaatgtttt atgcattatt taagcctgtc tctattgttg gaatttcagg     1380
tcattttcat aaatattgtt gcaataaata tccttgaaca ca                         1422

<210> SEQ ID NO 8
```

-continued

```
<211> LENGTH: 58
<212> TYPE: DNA
<213> ORGANISM: Artificial Sequence
<220> FEATURE:
<223> OTHER INFORMATION: Forward primer

<400> SEQUENCE: 8
ccggcaaatg agtacgaaga taaccctcga gggttatctt cgtactcatt tgtttttg        58

<210> SEQ ID NO 9
<211> LENGTH: 58
<212> TYPE: DNA
<213> ORGANISM: Artificial Sequence
<220> FEATURE:
<223> OTHER INFORMATION: Reverse primer

<400> SEQUENCE: 9
aattcaaaaa caaatgagta cgaagataac cctcgagggt tatcttcgta ctcatttg        58

<210> SEQ ID NO 10
<211> LENGTH: 58
<212> TYPE: DNA
<213> ORGANISM: Artificial Sequence
<220> FEATURE:
<223> OTHER INFORMATION: Forward primer

<400> SEQUENCE: 10 ccggggggaag atactgtgga gatgactcga gtcatctcca cagtatcttc cctttttg        58

<210> SEQ ID NO 11
<211> LENGTH: 58
<212> TYPE: DNA
<213> ORGANISM: Artificial Sequence
<220> FEATURE:
<223> OTHER INFORMATION: Reverse primer

<400> SEQUENCE: 11
aattcaaaaa gggaagatac tgtggagatg actcgagtca tctccacagt atcttccc        58

<210> SEQ ID NO 12
<211> LENGTH: 6
<212> TYPE: DNA
<213> ORGANISM: Artificial Sequence
<220> FEATURE:
<223> OTHER INFORMATION: Loop sequence

<400> SEQUENCE: 12 ctcgag                                                                    6
```